Figure 1:
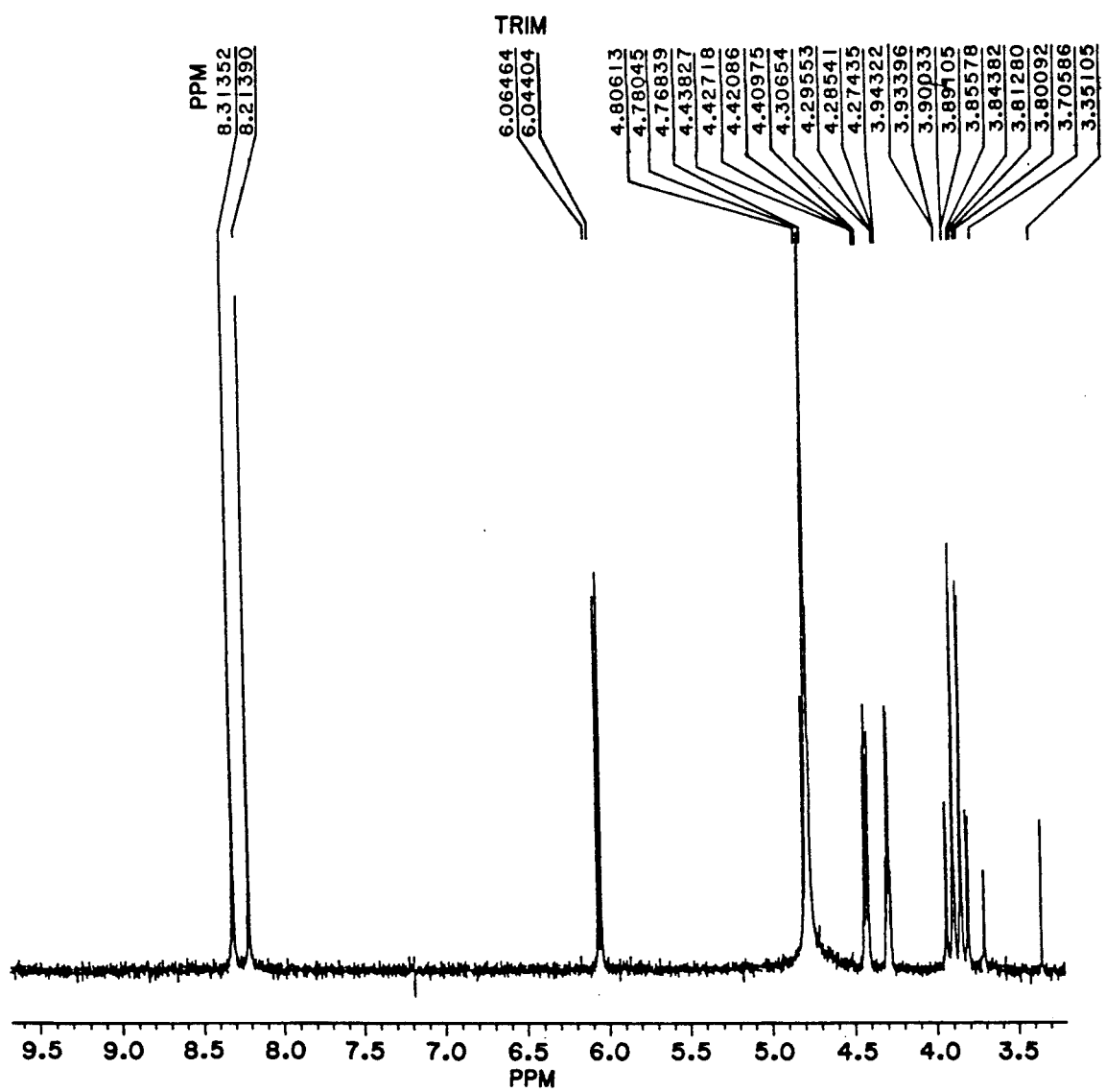

United States Patent [19]

Ries et al.

[11] Patent Number: 5,009,698

[45] Date of Patent: Apr. 23, 1991

[54] METHOD FOR STIMULATING PLANT GROWTH USING SYNTHETICALLY PRODUCED 9-BETA-1(+) ADENOSINE

[75] Inventors: Stanley K. Ries; Violet F. Wert; Muraleedharan G. Nair, all of East Lansing, Mich.

[73] Assignee: Board of Trustees operating Michigan State University, East Lansing, Mich.

[21] Appl. No.: 345,217

[22] Filed: Apr. 28, 1989

[51] Int. Cl.$^5$ .................. A01N 43/08; A01N 43/713; A01N 43/90

[52] U.S. Cl. .......................................... 71/92; 71/65

[58] Field of Search ......................... 71/79, 88, 92, 14

[56] References Cited

U.S. PATENT DOCUMENTS 4,150,970 4/1979 Ries et al. ............................. 71/122
4,741,754 5/1988 Ries ........................................ 71/79

OTHER PUBLICATIONS

Ries (II) International Symposium on Triacontanol, Nov. 25-28, Zhenjiang China, Shanghai Institute of Plant Phys. Acad. Sinica (1987).
Antonin Holy, Nucleic Acid Chemistry, J. Wiley & Sons, N.Y. Article No. 92, part 1: 527–532 (1978).
Cusack et al., Proc. R. Society, London, Ser. B. 206 (1163) 139–144 (1979).
Ries, Critical Reviews in Plant Sciences 2: 239–285 (1985).
Ries et al., Science 195: 1339–1341 (1977).
Lim, ung–Kyu, Korean J. Ecol. 4:1 (1982).
Devakumar et al., Indian J. Agr. Sci. 56: 744–747 (1986).
Ries et al., J. Plant Growth Regulation 1: 117–127 (1982).
Lesniak et al., Physiol. Plant 68: 20–26 (1986).
Jones et al., Planta 144: 277–292 (1979).
Jurovcik et al, Febs Letters 18: 274–276 (1971).

Primary Examiner—Richard L. Raymond
Assistant Examiner—B. Bembenick
Attorney, Agent, or Firm—Ian C. McLeod

[57] ABSTRACT

A method for stimulating plant growth using synthetically produced 9-beta-L(+) adenosine is described. The method uses the synthetically produced compound instead of a naturally occurring material which occurs in only minute amounts and is difficult to isolate.

7 Claims, 9 Drawing Sheets

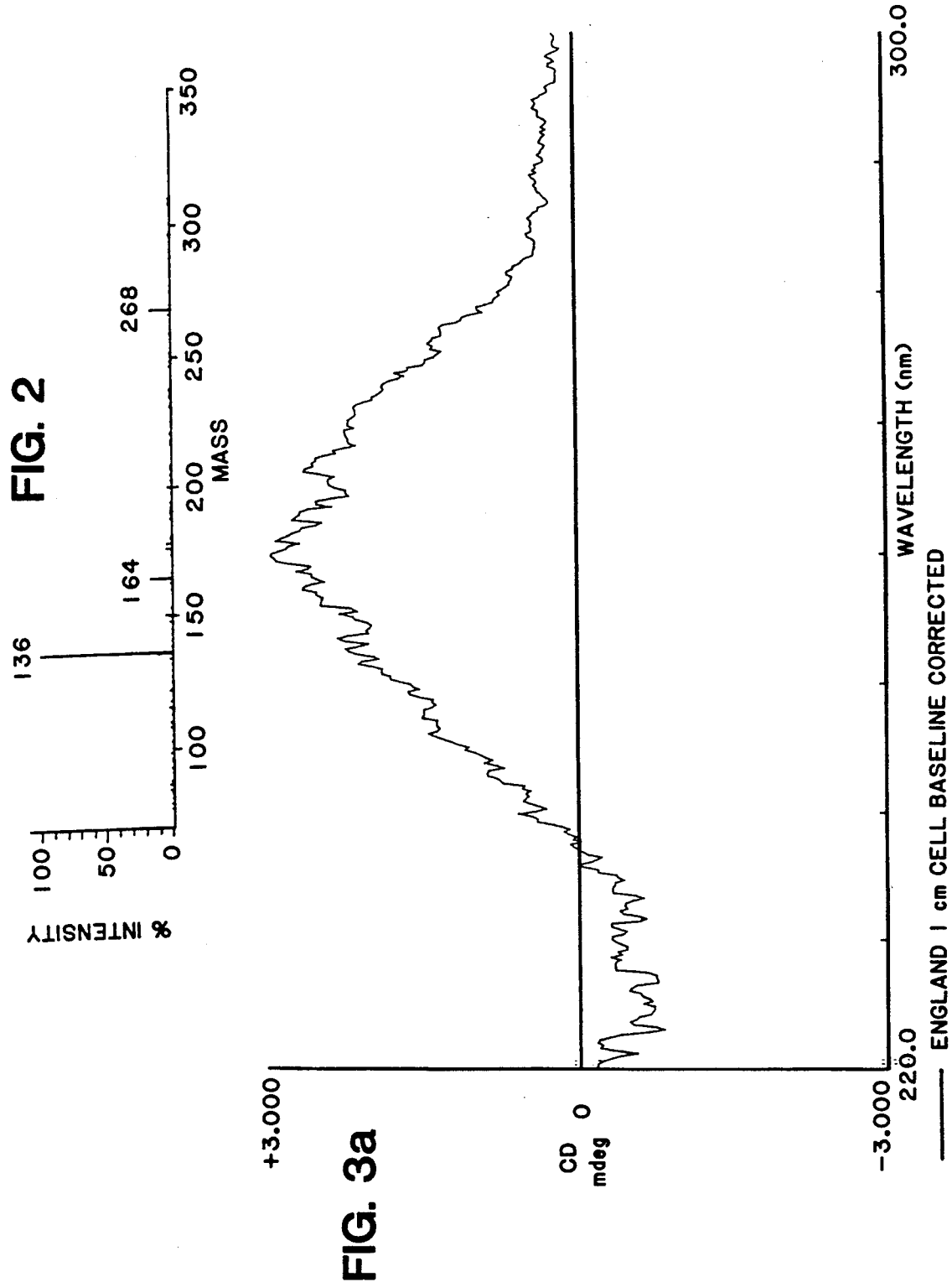

METHOD FOR STIMULATING PLANT GROWTH USING SYNTHETICALLY PRODUCED 9-BETA-1(+) ADENOSINE

BACKGROUND OF THE INVENTION

1. Field of the Invention

The present invention relates to the use of chemically produced (synthetic) 9-beta-L(+) adenosine to stimulate plant growth. In particular, the present invention relates to the use of very small amounts of the chemically produced 9-beta-L(+) adenosine for this purpose.

2. Prior Art

Triacontanol (TRIA), a C30 primary alcohol and a natural constituent of plant waxes, increases the growth and sometimes the yield of many crop species as described in U.S. Pat. No. 4,150,970 to Ries et al; Ries, S. K., Critical Reviews in Plant Sciences 2:239–285 (1985); and Ries, S. K., Wert, V. F., Sweeley, C. C. and Leavitt, R. H., Science 195:1339–1341 (1977)). It is also used on several million acres of tea, vegetable and agronomic crops in Asia each year to increase yield as described in Abstracts, International Symposium on Triacontanol, November 25–28, Zhenjiang, China, Shanghai Institute of Plant Physiology, Academia Sinica (1987); Lim, ung-Kyu, Korean J. Ecol. 4:1 (1982); and Devakumar, C., Baskaran, S., and Mukerjee, S. K. Indian J. Agr. Sci. 56:744–747 (1986).

Increases in leaf area, dry weight, total Kjeldahl nitrogen, water soluble protein, reducing sugars, and free amino acids have been measured within 40 minutes of TRIA application to maize and rice seedlings as described in Ries, S. K., Critical Reviews in Plant Sciences (1985) cited previously and Ries, S. K. and Wert, V. F., J. Plant Growth Regulation 1:117–127 (1982). Both $Ca^{2+}$ and $Mg^{2+}$ dependent ATPase activity increased by 40–60% within 30 minutes of the addition of 2.3 nm of TRIA to cell-free extracts from barley (*Hordeum vulgare*) roots as described in Lesniak, A. P. and Ries, S. K. Physiol. Plant. 68:20–26 (1986). Equimolar concentrations of octacosanol (OCTA, $C_{28}$ primary alcohol), as well as other long chain alcohols, inhibited the activity of TRIA as described in Jones, J., Wert, V. F. and Ries, S. K. Planta 144:277–292 (1979), even if the two chemicals were applied separately to the shoots and roots, but only when these long chain alcohols were applied prior to TRIA as described in Ries, S. K. Critical Reviews in Plant Sciences (1985) cited previously and Jones, J., Wert, V. F. and Ries, S. K., Planta (1979) cited previously.

Thus triacontanol (TRIA) as described in U.S. Pat. No. 4,150,970 to Ries et al increases the dry weight and alters the metabolism of rice (*Oryza sativa L.*) and maize (*Zea mays L.*) seedlings, within 10 minutes of application of 1.0 µg/L (see also Ries, S. K., Critical Reviews in Plant Sciences (1985) cited previously. Application of OCTA to either rice roots or shoots 1 minute prior to application of TRIA to the opposite part of the seedling inhibits this response as discussed in Ries, S. K., Critical Reviews in Plant Sciences (1985) previously cited; and Jones, J., Wert, V. F. and Ries, S. K., Planta (1979) previously cited.

As described in U.S. Pat. No. 4,741,754 to Ries, which is incorporated herein by reference and made a part hereof, TRIA quickly elicits a second messenger, referred to as TRIM, which moves rapidly throughout the plant resulting in stimulation of growth (dry weight increase) and water uptake. OCTA also produces a second messenger (OCTAM) that inhibits TRIA activity, but not the activity of TRIM. The same procedure used to extract TRIM when used on control plants not treated with TRIA, yielded a compound which had no affect on plant growth. Melting point, infrared (IR), mass spectroscopy (MS), and nuclear magnetic resonance spectroscopy (NMR) produced the result that both TRIM and tallow alkyl sulfate (TAS) appeared to be identical. However, these compounds showed remarkable differences in biological activity. For a long time, TRIM has eluded chemical identification and synthesis of the active ingredient.

TRIM is extracted and purified from plant material in only minute quantities after application of TRIA to a plant, as described in U.S. Pat. No. 4,741,754 to Ries. There is a need for a synthetically derived, pure material in view of the large amounts necessary for plant growth stimulation at a commercial level.

OBJECTS

It is therefore an object of the present invention to provide a method of plant growth stimulation using synthetically prepared, 9-beta-L(+) adenosine which is at least as effective as naturally derived TRIM and in some instances is significantly more effective. These and other objects will become more apparent to those skilled in the art from the following description and the drawings.

IN THE DRAWINGS

Figure 1A:
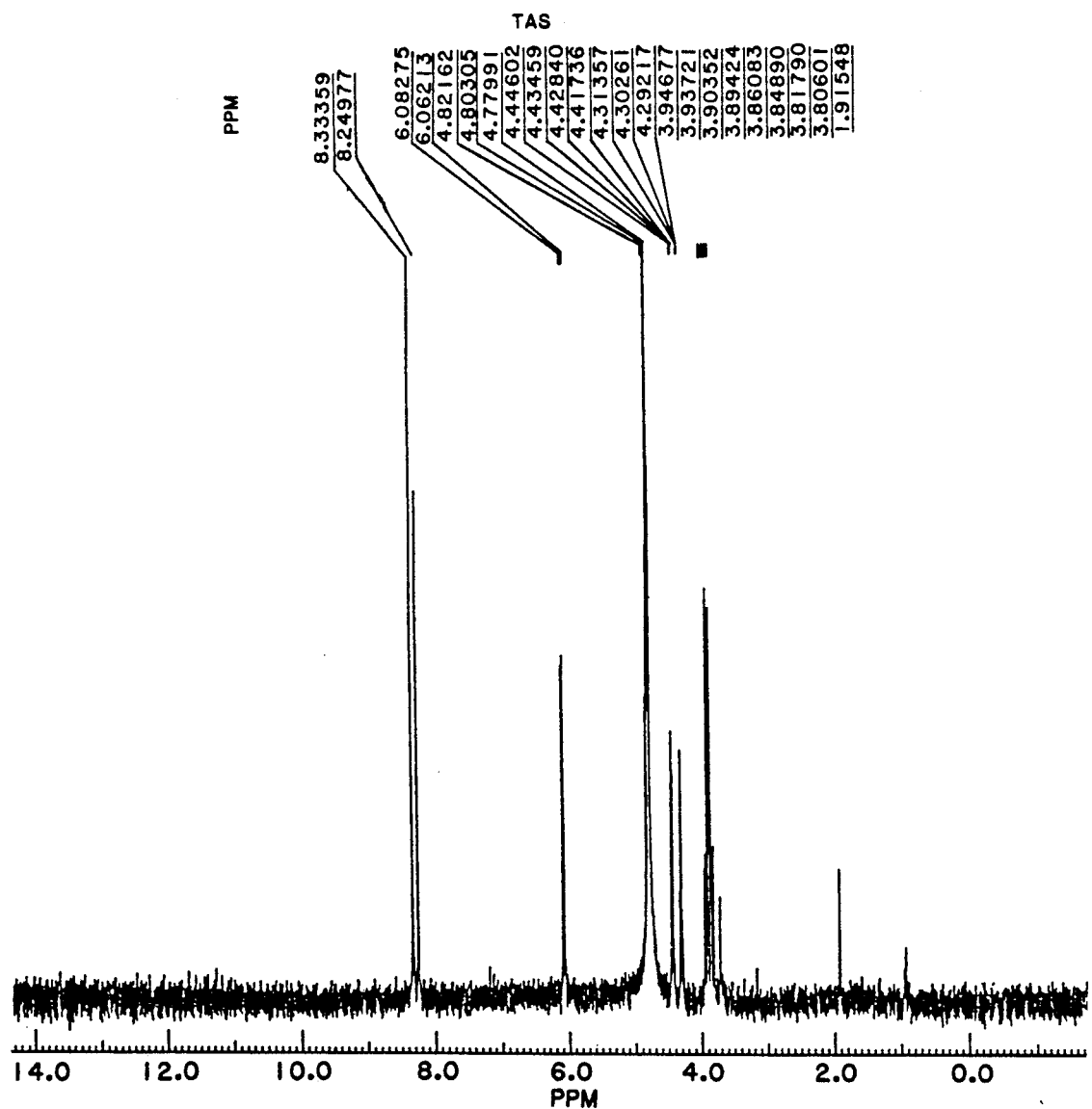

FIGS. 1 and 1A are a $^1$H NMR spectrum (300 MHZ, $CD_3$ OD) of naturally derived 9-beta-L(+) adenosine (TRIM) and 9-beta-D(−) adenosine (TAS, respectively). Similar spectra to TRIM were obtained for the synthetically derived 9-beta-L(+) adenosine.

FIG. 2 is a chemical ionization mass spectrograph (MS) of naturally derived TRIM. Similar MS spectra were obtained for naturally derived TAS, synthetically prepared 9-beta-D(−) adenosine and synthetically prepared 9-beta-L(+) adenosine.

Figure 3B:
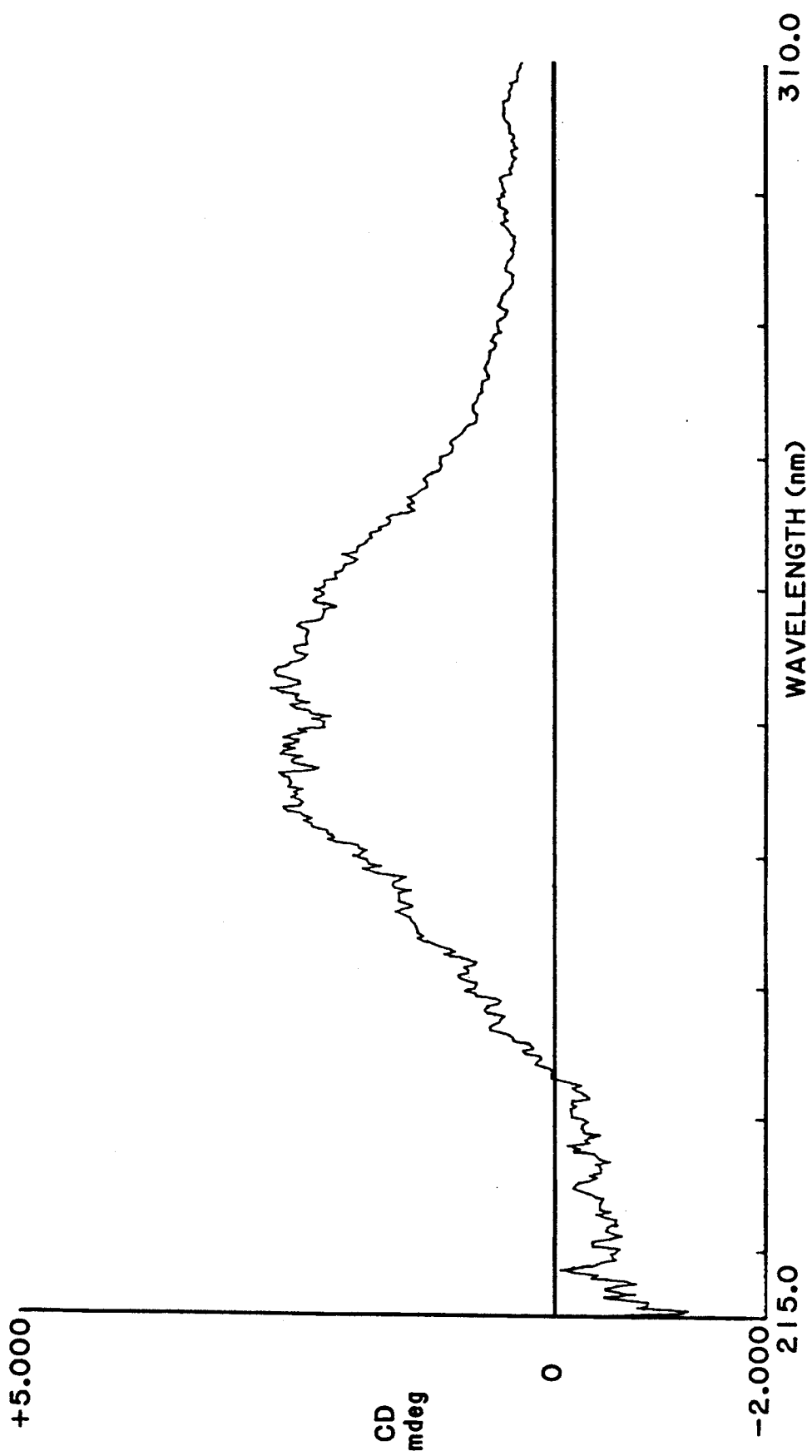
Figure 3C:
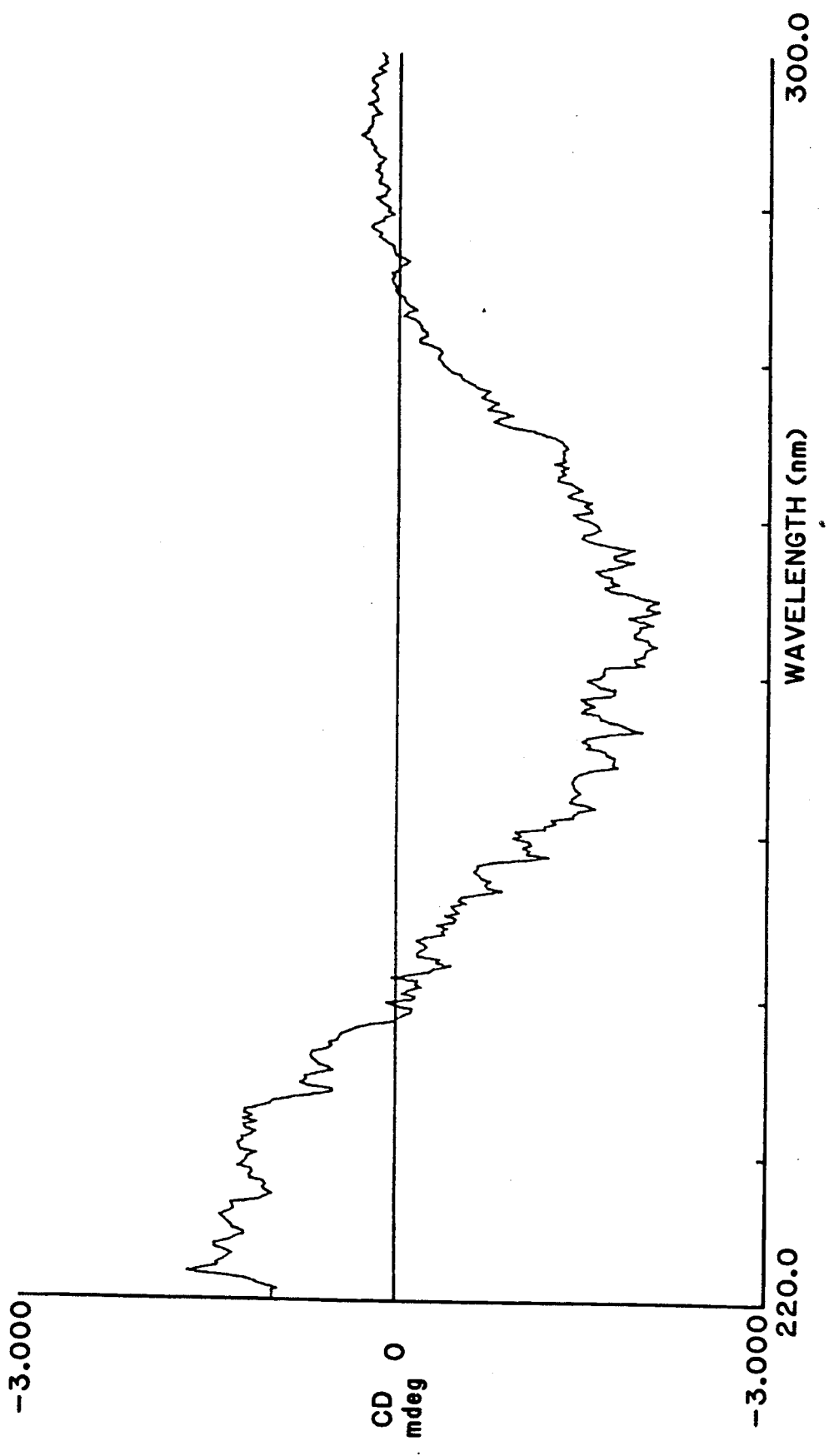
Figure 3D:
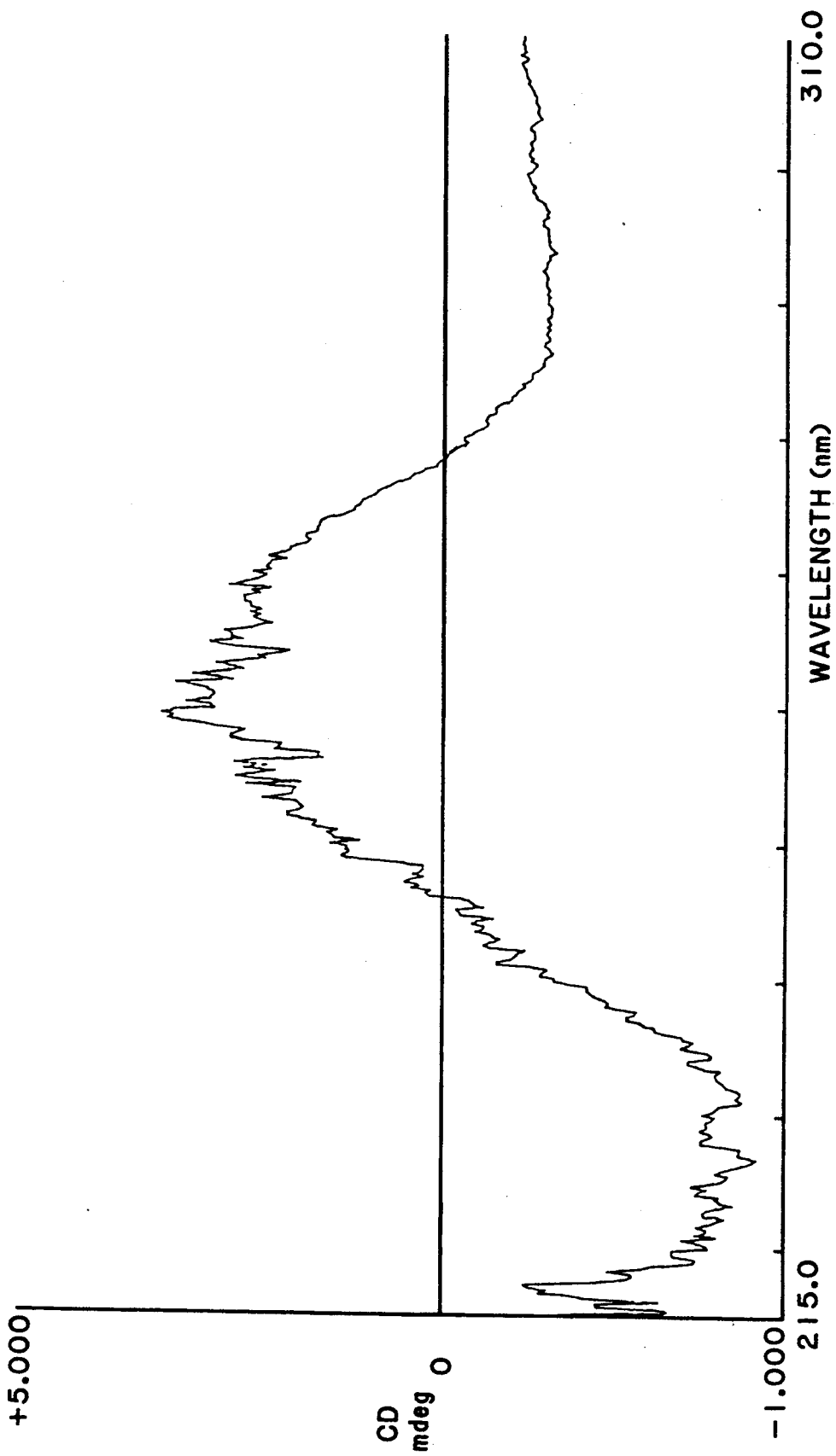
Figure 3E:
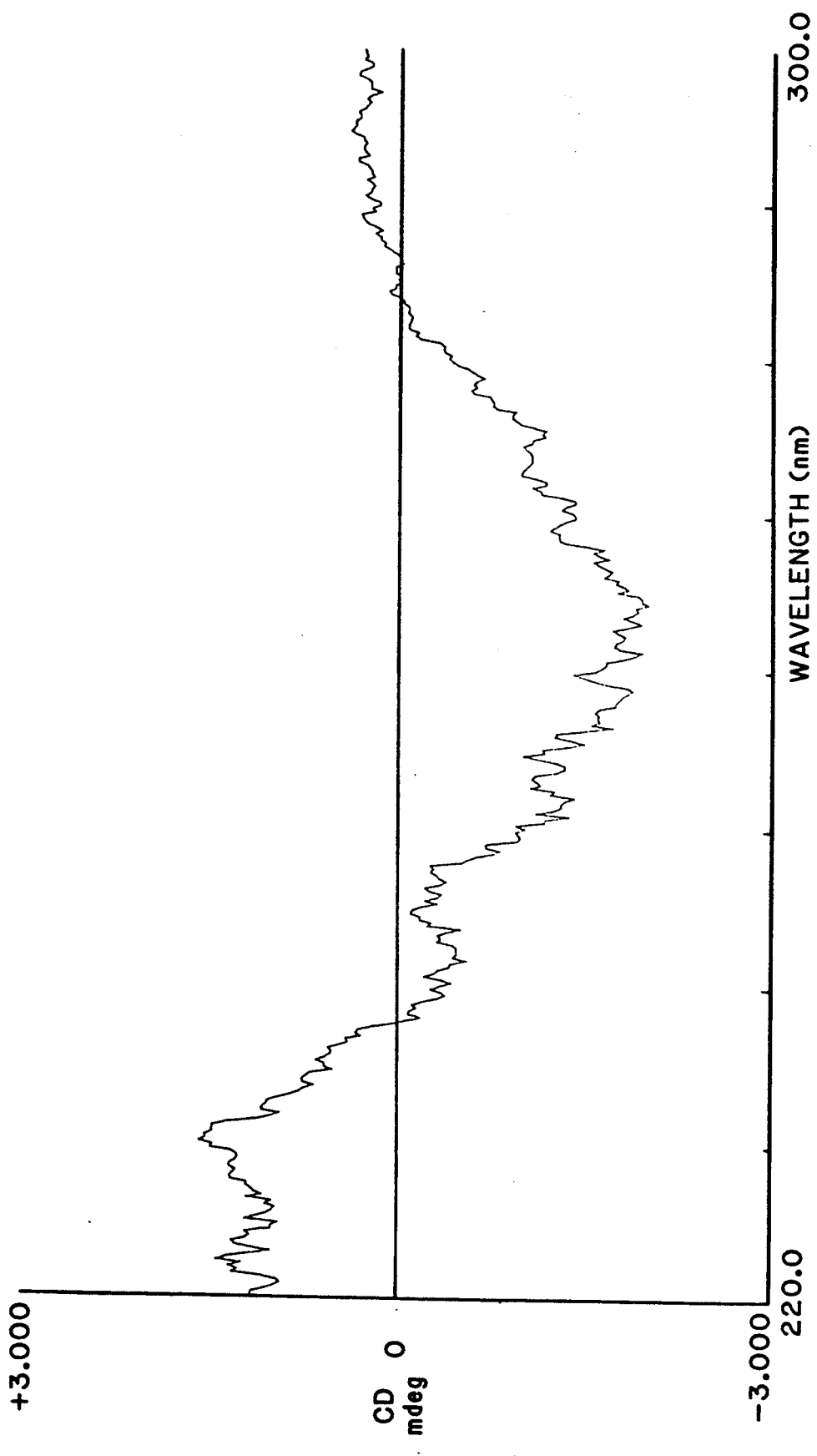
Figure 3F:
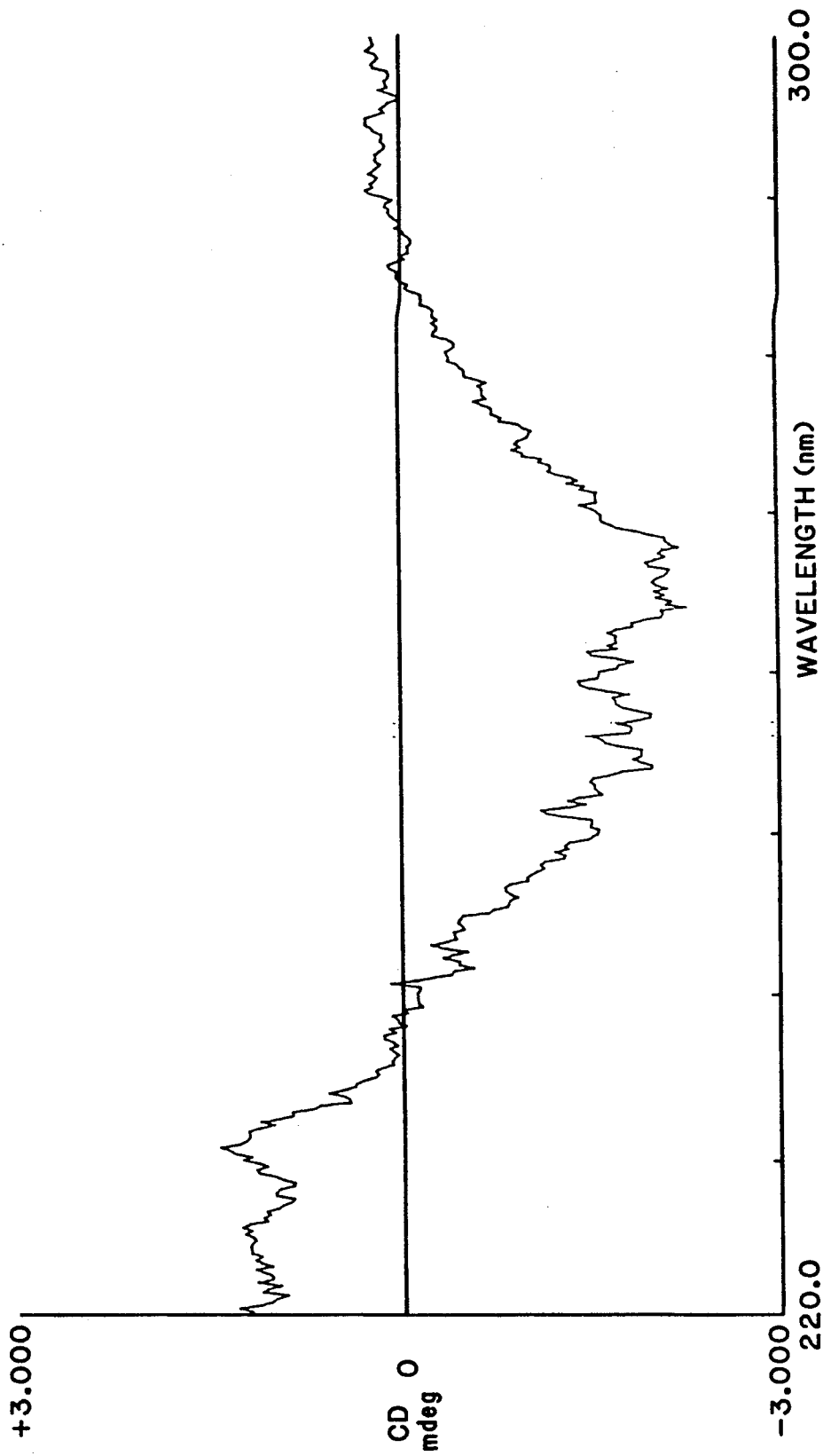
Figure 3G:
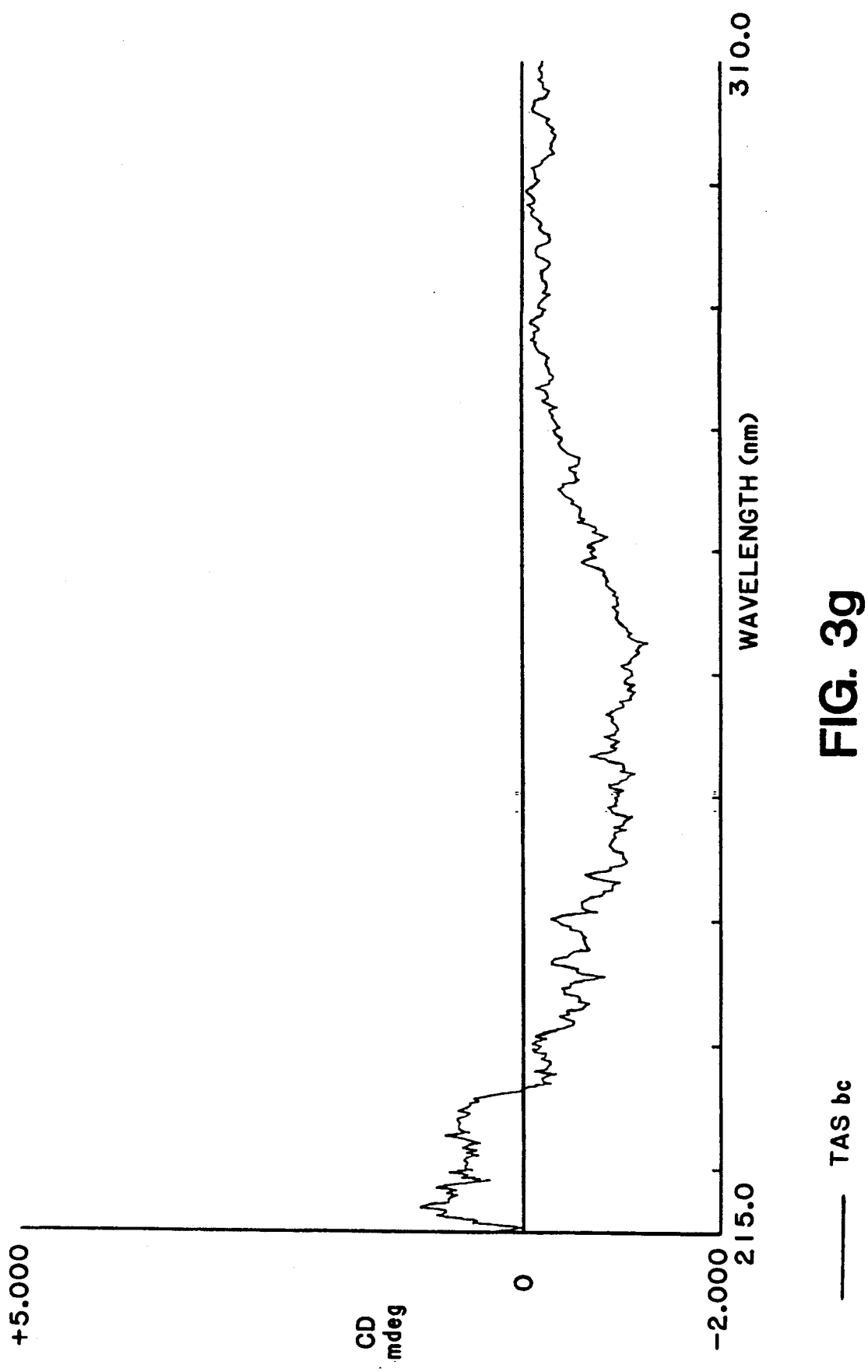

FIGS. 3a to 3g show circular dichroism (CD) of naturally derived TAS, naturally derived TRIM and synthetically prepared 9-beta-L(+) adenosine with and without purification using adenosine deaminase to eliminate 9-beta-D(−) adenosine as an impurity which inhibits effectiveness. FIGS. 3a and 3b show purified 9-beta-L(+) adenosine. FIG. 3c shows TRIM after purification with adenosine deaminase. FIG. 3d shows TRIM before treatment with the adenosine deaminase. FIG. 3e shows the impure 9-beta-D(−) adenosine after treatment with adenosine deaminase and re-purification and FIG. 3f shows the results before. FIG. 3f and 3g show TAS before and after treatment with adenosine deaminase.

GENERAL DESCRIPTION

The present invention relates to a method for stimulating the growth of a plant which comprises: applying an effective amount of synthetically prepared, 9-beta-L(+) adenosine to the plant in order to stimulate growth of the plant. The adenosine may be substantially free of other compounds which inhibit plant growth stimulation. The amount used is preferably between about 0.01 to 100 micrograms per liter in an aqueous solution which is applied to the plant (roots, shoot or leaves) in order to wet the surfaces.

In U.S. Pat. No. 4,741,754 to Ries, which is incorporated herein by reference and made a part hereof, TRIM was not chemically identified and it was expensive to extract. The present invention thus identifies the active compound and provides a process for its synthesis. As shown in U.S. Pat. No. 4,741,754, water-soluble TRIM extracted in minute amounts from the roots of 13-18 day-old rice plants, whose shoots were sprayed with 1.0 micrograms/L TRIA, increased the growth of rice seedlings about 50% more than similar extracts from untreated plants, within 24 hours of application. Both OCTA and OCTAM inhibited the activity of TRIA but not of TRIM. TRIM was isolated from rice roots within 1 minute of a foliar application of TRIA and found in rice roots connected to their cut shoots by a 4 mm column of water (latex tubing). TRIM was also recovered in minute amounts from water in which cut stems of TRIA-treated plants had been immersed, but not in water in which untreated or surfactant treated cut stems were immersed.

As used in the present description, the terms TRIM and TAS refer to the naturally derived materials. The synthetically derived compounds are characterized as such.

Synthetic 9-beta-L(+) adenosine can be incorporated in various agriculturally acceptable, non-interfering carriers particularly water, water with surfactants as well as other organic material and/or mixtures. Such carriers are well known to those skilled in the art and may consist, for instance, of powdered clays, silicates, celluloses and the like. The products can be sprayed or dusted on the plants. Also contemplated are slow release pellets which release the synthetic 9-beta-L(+) adenosine over time. U.S. Pat. No. 4,741,754 describes various formulations.

The 9-beta-L(+) adenosine can be synthetically prepared in pure form in large amounts by the process of Antonin Holy, Nucleic Acid Chemistry J. Wiley & Sons, New York, Article No. 92, part 1: 527-532 (1978). Cusack, N. J., Hickman, M. E. and Born, G.V.R., Proc. R. Soc. London, Ser. B 206 (1163) 139-144 (1979) also describes a process for preparing this compound. Adenosine deaminase is used to eliminate 9-beta-D(−) adenosine which forms inosene.

SPECIFIC DESCRIPTION

Examples 1 and 2 show the isolation and purification of TRIM and the characterization of the purified compound as 9-beta-L(+) adenosine, which is available commercially as a synthetically derived compound, although generally requiring purification to eliminate impurities. Tests show that the synthetic, pure 9-beta-L(+) adenosine is more effective than TRIM. Comparative Example 3 shows the affect of synthetically derived 9-beta-D(−) adenosine and other chemicals on rice plants versus TRIM or synthetic 9-beta-L(+) adenosine. Example 4 shows the treatment of corn and Example 5 shows the treatment of cucumbers.

In the following Examples 1 to 3, rice (cv M-101, U of Calif.) plants were grown as described in U.S. Pat. No. 4,741,754 to Ries. For each test for activity, seedlings were grown in test tubes (14.5 cm×2.4 cm) for 24 hours containing 0.5 strength nutrient solution (20 ml), at 30° C. day and 25° C. night temperatures, with a 16 hour photoperiod (PAR 300-350 mol $S^{-1}m^{-2}$). The observed variance due to plant size was assigned to blocks in the experimental design. All treatments were randomized within blocks using a random number table, prior to and after spraying and placing them back in the growth chamber. All data were subjected to analysis of variance and compared using F tests for trend effects, or the LSD for mean separations.

EXAMPLE 1

To obtain purified TRIM for chemical identification, the foliage of 21 24-day-old rice seedlings was sprayed with TRIA (1.0 μg/L) formulated as a colloidal dispersion as described by Laughlin, R. G., Munyon, R. L., Ries, S. K. and Wert, V. F., Science 219:1219-1221 (1983). Control seedlings were sprayed with 0.01 μg/L tallow alkyl sulfate (TAS), the concentration of the surfactant used in the formulation. The roots were removed after 100 minutes, weighed and frozen until extracted. The frozen roots (20 μg) were extracted with methanol in a soxhlet (150 ml for 2 hours) and the extract was dried in vacuo. The residue was redissolved in water (20 ml), centrifuged (7900 rpm) and the resulting supernatant was evaporated to dryness at reduced pressure. Preliminary purification of this extract was achieved with a flash column (35 cm×20 mm, $C_{18}$ bonded silica gel, 40 μm) using $MeOH-H_2O$ (30:70 v/v) as the eluant at 2 ml/min flow rate. Twenty fractions were collected in 5 ml portions. Bioassays with rice plants showed activity only in fractions 6-14. These fractions, containing the active compound TRIM, were combined and evaporated to dryness. A similar flash column purification of the control (TAS) extract and the rice bioassay of the fractions indicated no activity.

The above fractions, TRIM and TAS, were purified by HPLC on a preparative $C_{18}CN-H_2O$ (80:20 v/v, 2 ml/min) at 60° C. The fraction which eluted at 22.1 min was further purified again in the same solvent, for both TRIM and TAS, as above. The final HPLC purification was performed on the same column using $CH_3OH-H_2O$ (30:70 v/v, 4 ml/min) at 25° C. The fraction collected at 19.4 minutes was evaporated to dryness in vacuo. The resulting materials were identified as TRIM from the experimental roots and as TAS for the inactive compound from the control roots.

Recrystallization of purified TRIM and TAS from MeOH yielded colorless crystals with identical melting points, 230°-234° C. (determined on a Kofler hot stage apparatus and are uncorrected). Both compounds gave identical $^1H$- (FIG. 1) and $^{13}C$-NMR spectra. A mixed $^1H$-NMR spectrum of TRIM and TAS were superimposable to the individual proton spectra. Identical CI and FAB MS (FIG. 2) gave (M+H) at m/z 268 for purified TRIM and TAS and was in agreement with the NMR data. These results made it difficult to identify TRIM.

TRIM and TAS were finally identified as containing 9-beta adenosine. The only analytical difference between TRIM and TAS was in their circular dichroism (CD) obtained on a JASCO Model J600 spectrophotometer (FIGS. 3a to 3h). Spectral comparison of commercially available 9-beta-D(−) adenosine to purified TRIM and TAS confirmed the structures of the purified TAS and purified TRIM to be 9-beta-D(−) adenosine and 9-beta-L(+) adenosine, respectively.

Purified TRIM and synthetic 9-beta-L(+) adenosine prepared by the process described by Cusack, N. J., Hickman, M. E. and Born, G. V. R., Proc. R. Soc. London, (1979)) cited previously and treated with adenosine deaminase were identical in every respect including the biological activity on rice plants as shown in the following Table 1.

TABLE 1

Response of 17-day-old rice seedlings to TAS Control, 9-beta-D(-) adenosine, purified TRIM (9-beta-L(+) adenosine, synthetically derived 9-beta-D(-) adenosine and synthetically derived 9-beta-L(+) adenosine.

| Chemical (10.0 µg/L) | Increase in 24 hours | |
|---|---|---|
| | Dry Weight (mg/plant) | Water uptake (ml/plant) |
| Control (no treatment) | 7.00 | 4.48 |
| TAS control | 7.24 | 4.77 |
| Purified TRIM | 13.44 | 5.18 |
| Yeast Derived[1] 9-beta-D(−) adenosine | 7.60 | 4.84 |
| Synthetic, 9-beta-L(+) adenosine[1] | 13.44 | 5.20 |
| LSD 5% | 1.91 | 0.28 |
| LSD 1% | 2.58 | 0.38 |

[1] Sigma Chemicals located in St. Louis, Missouri.

When the compositions of Table 1 were tested using the rice bioassay with a foliar application of TRIM at 100 µg/L (10 times Table 1), TRIM and 9-beta-L(+) adenosine significantly increased water uptake and dry weight after 20 hours. The net dry weight gain was 8.45, 6.98 and 13.04 mg/whole plant, for control, TAS and TRIM, respectively, over plants which weighed 38.70 mg at the start of the test. The synthetic 9-beta-L(+) adenosine produced equivalent results. The F value for comparison of TRIM with the other two treatments was significant at 1% level.

In three extraction regimes with different sets of treated and control plants, the average yield of purified TRIM from rice roots of 21-24-day-old plants was approximately 124 µg/g dry weight of roots. The yield of adenosine from TAS (control) plants was about 96 µg/g dry weight of roots. Thus, large numbers of plants are required for the extraction to produce very small amounts of TRIM. The synthetically derived material may be prepared in large amounts.

EXAMPLE 2

9-beta-L(+) adenosine from various sources was checked for purity by reacting it with adenosine deaminase which reacts selectively with 9-beta-D(−) adenosine to produce D-inosine. The 9-beta-L(+) adenosine was not affected by this enzyme. The results are shown in Table 2a.

TABLE 2a

Quantity of 9-beta-L(+) adenosine remaining based on HPLC analysis after exposure of different sources of adenosine to adenosine deaminase which is specific for 9-beta-D(−) adenosine. There was 100 µg of sample/100 µl of water containing 0.1 unit of enzyme.

| Source of adenosine | Time in Hours Percent 9-beta-L(+) adenosine | | | |
|---|---|---|---|---|
| | 2 | 4 | 6 | 8 |
| 9-beta-D(−)[1] | 0.55 | 0.45 | 0.47 | — |
| 9-beta-L(+)[2] | 100.0 | 100.0 | 100.0 | 99.83 |
| TAS control | 0.57 | 0.52 | 0.67 | 0.57 |
| TRIM | 6.02 | 5.73 | 5.85 | 5.63 |

[1] Sigma Chemicals, St. Louis, Missouri.
[2] Cusack et al, cited previously.

The products after 8 hours were tested for circular dichroism (CD). FIG. 3a shows known pure 9-beta-L(+) adenosine as prepared by Cusack et al. FIG. 3b shows TRIM after treatment with adenosine deaminase. FIG. 3c shows TRIM before treatment with adenosine deaminase. FIG. 3d shows a commercial 9-beta-D(−) adenosine after treatment with adenosine deaminase. FIG. 3e shows the commercial adenosine of FIG. 3d before treatment with adenosine deaminase. FIG. 3f shows TAS after treatment with adenosine deaminase and FIG. 3g shows TAS before treatment with adenosine deaminase.

As can be seen from Table 2a and FIGS. 3a to 3g, commercially available 9-beta-D(−) adenosine contains some 9-beta-L(+) adenosine and is very impure. Likewise, TRIM, which was thought to be pure, is very impure. Even though several chiral columns were tested, TRIM could not be further purified without using the adenosine deaminase followed by further HPLC. But for the use of the enzyme, TRIM could not have been further purified using known HPLC techniques.

The pure 9-beta-L(+) adenosine has thus been found to be as effective as the impure TRIM of U.S. Pat. No. 4,741,754 at higher concentrations.

Table 2b shows the response of 16-day-old rice seedlings to adenosine from different sources after incubation with adenosine deaminase and purification by HPLC.

TABLE 2b

| Adenosine Source (1.0 µgL) | Increase in 24 hours Dry Weight | |
|---|---|---|
| | (mg/plant) | (% of Control) |
| None | 8.16 | |
| Untreated roots | 7.66 | 94 |
| TAS Control | 8.78 | 108 |
| TRIM | 13.69 | 168 |
| Synthetic L(+) adenosine | 13.80 | 169 |
| Commercial D(−) adenosine* (incubated with adenosine deaminase) | 11.60 | 142 |
| LSD 5% | 1.90 | |
| LSD 1% | 2.55 | |

*This indicates that the commercial material contains significant amounts of L(+) adenosine which remains.

COMPARATIVE EXAMPLE 3

Adenosine hemisulfate salt, adenine 9-beta-D-arabinosutanoside, adenosine 5'-diphosphoglucose dipotassium, adenosine-5'-monophosphate, adenosine-3' monophosphoric acid monohydrate, adenosine 5 triphosphate, and adenosine 3', 5 cyclic monophosphoric acid sodium salt were not active in the rice bioassay, at concentrations of at least 100 µg/L and did not cochromatograph with purified TRIM and TAS.

Synthetically derived 9-beta-D(−) adenosine was active (increased dry weight) in several rice bioassays. However, it never increased growth as much as or at as low a concentration as purified TRIM (1.0 µg/L) when all three were compared in the same test. Since 9-beta-D(−) adenosine from TAS (control plants) did not show significant activity, even when applied at 100 times the concentration of TRIM as shown in Table 3, and the synthetic 9 beta-D(−) adenosine was never as active as the TRIM, the results were suspicious. It was found that synthetic 9-beta-D(−) adenosine contained some of the 9-beta-L(+) adenosine enanthiomer as can be seen from Example 2.

TABLE 3

Growth of 15-day-old rice seedlings treated with purified TAS, 9-beta-D(−) adenosine and TRIM.

| (Chemical) | (µg/L) | Increase in 19 hours (mg DW/plant) |
|---|---|---|
| 0 | 0 | 3.87 |
| TAS | 10 | 3.79 |

TABLE 3-continued

Growth of 15-day-old rice seedlings treated with purified TAS, 9-beta-D(−) adenosine and TRIM.

| (Chemical) | (μg/L) | Increase in 19 hours (mg DW/plant) |
|---|---|---|
| TAS | 1000 | 3.19 |
| TRIM | 10 | 8.44a |
| LSD 5% | | 3.51 | aF value for comparison with other treatments significant at 1% level (F = 12.4).

Equivalent results to TRIM are achieved with synthetically derived 9-beta-L(+) adenosine in this test. Table 4 shows the results on rice seedlings using 9-beta-L(+) adenosine which was substantially pure in that it had been treated with adenosine deaminase as compared to TRIM.

TABLE 4

A comparison of the response of 17-day-old rice seedlings to different concentrations of synthetically derived 9-beta-L(+) adenosine and TRIM. The test is an average of 2 experiments with 5 replications each. The average dry weight of the zero time was 33.55 mg for TRIM and 33.36 for the synthetic 9-beta-L(+) adenosine.

| Concentration (μg/L) | TRIM DW | % increase over control | Synthetic DW | % increase over control |
|---|---|---|---|---|
| 0 | 6.95 | — | 5.77 | |
| .0001 | 7.83 | 13 | 7.46 | 29 |
| .01 | 8.19 | 18 | 8.19 | 55 |
| 1.00 | 9.72 | 40 | 9.89 | 71 |
| 100.0 | 11.34 | 63 | 9.08 | 55 |
| LSD 5% | 1.87 | | 1.95 | |
| LSD 1% | 2.51 | | 2.61 | |

The results clearly show that the synthetic, pure adenosine is much more effective than TRIM in concentrations between about 0.0001 and 1.0 micrograms per liter.

EXAMPLE 4

Table 5 shows the response of '3780' field corn seedlings to applications of L(+) adenosine applied one week after planting and harvested six days after treatment in greenhouse.

TABLE 5

| L(+) adenosine (μg/L) | Dry weight (mg/shoot) | % increase over control |
|---|---|---|
| Control | 402 | |
| 0.01 | 478a | 19 |
| 1.00 | 438 | 9 |
| 100.00 | 438 | 9 |
| 10000.00 | 445 | 11 | aF value for difference from control significant at 5% level.

This test shows a significant increase over the control using 9-beta-L(+) adenosine, particularly at very low concentrations.

EXAMPLE 5

Table 6 shows the response of cucumbers to L(+) adenosine applied at two times when cucumbers grown under two light intensities in the greenhouse, the adenosine and control sprayed with six molar urea. The adenosine was dissolved in urea to prevent bacterial breakdown. Sprays were applied 12 and 17 days after planting and shoots harvested 22 days after planting.

TABLE 6

| | Light intensity (moles/m$^2$/sec) | | | |
|---|---|---|---|---|
| 9 + beta-L(+) adenosine μg/liter | Low[b] (120) | High[b] (320) | Average[a] | % increase over control |
| | Dry weight mg/plant | | | |
| 0 | 490 | 717 | 604 | |
| 0.01 | 483 | 800 | 742 | 5% |
| 1.00 | 543 | 770 | 656 | 9% |
| 100.00 | 480 | 823 | 652 | 8% |

[a]F value for control vs. treatment significant at 5% level.
[b]F value for low light vs. high light × the cubic trend significatn at 5% level.

This test shows a significant increase using 9-beta-L(+) adenosine over the control. Various known antibacterial agents can be used in the composition so long as they do not interfere with the growth stimulation.

In the same manner, soybeans, wheat, sorghum and barley, as well as other grains are treated with between about 0.01 and 100 μg/L of 9-beta-L(+) adenosine to produce an increase in dry weight.

It has been found that TRIA is a very lipophillic compound which acts on cell membranes to produce TRIM in minute amounts which is rapidly translocated throughout the plant causing a cascade of metabolic events, resulting in the observed increase in soluble protein, reducing sugars, and dry weight. Since 9-beta-L(+) adenosine has not been found yet in control plants or reported in the literature, it is believed that adenosine present on the plant membrane contains an open-chain ribose moiety. This may be changed to the 9-beta-L(+) adenosine by the TRIA acting on a membrane bound enzyme, and to 9-beta-D(−) adenosine in TRIA's absence. Other long chain alcohols applied to the opposite part of the plant also elicit second messengers which stop the formation of 9-beta-L(+) adenosine within 1 minute as discussed in Ries, S. K., Critical Reviews in Plant Sciences (1985) cited previously. Thus, the enantiormerization of 9-beta-adenosine into 9-beta-L(+) adenosine elicited by TRIA and the inhibition of this activity by other long chain alcohols indicates the presence of a previously unknown growth regulation system in plants.

The present invention provides a method for greatly expanding the amount of plant growth produced per acre. The fact that 9-beta-L(+) adenosine is active in plants is unexpected in view of the fact that this compound is inactive in mammals and bacterial cells as shown by Cusack et al, discussed previously, and Jurovcik et al Febs Letters 18: 274 to 276 (1971).

All sorts of plants can be treated by the method of the present invention. The range of treatment is at least as wide as with TRIA and TRIM.

As used herein, the term "synthetic" means that the 9-beta-L(+) adenosine is produced by an in vitro process or method as opposed to an in vivo process in the plant. The process or method can be an entirely chemical synthesis or it can be a synthesis involving living cells such as a bacterial process for a particular step. It is intended that the foregoing description be only illustrative of the present invention and that the invention be limited only by the hereinafter appended claims.

I claim:

1. A method for stimulating the growth of a plant which comprises: applying an effective amount of synthetically prepared 9-beta-L,(+) adenosine to the plant in order to stimulate growth of the plant.

2. The method of claim 1 wherein the 9-beta-L(+) adenosine is substantially pure.

3. The method of claim 1 wherein the plant is a rice seedling.

4. The method of claim 1 wherein the 9-beta-L(+) adenosine is applied in an aqueous solution.

5. The method of claim 4 wherein the aqueous solution contains between about 0.0001 and 100 micrograms per liter of the 9-beta-L(+) adenosine.

6. The method of claim 1 wherein the 9-beta-L(+) adenosine is combined with an agriculturally acceptable carrier.

7. The method of claim 1 wherein an antibacterial agent is admixed with the adenosine.

* * * * *